United States Patent [19]
Toepfl

[11] 3,942,971
[45] Mar. 9, 1976

[54] DITHIOPHOSPHATES AND THEIR USE AS HERBICIDES

[75] Inventor: Werner Toepfl, Basel, Switzerland

[73] Assignee: Ciba-Geigy AG, Basel, Switzerland

[22] Filed: June 17, 1974

[21] Appl. No.: 479,731

Related U.S. Application Data

[60] Division of Ser. No. 320,338, Jan. 2, 1973, Pat. No. 3,833,600, which is a continuation-in-part of Ser. No. 160,898, July 8, 1971, abandoned, and a continuation-in-part of Ser. No. 160,897, July 8, 1971, abandoned, which is a continuation-in-part of Ser. No. 782,736, Dec. 10, 1968, abandoned.

[30] Foreign Application Priority Data
Dec. 3, 1967  Switzerland.................17542/67
July 25, 1968  Switzerland.................11206/68

[52] U.S. Cl. .................................................. 71/87
[51] Int. Cl.² ........................................ A01N 9/36
[58] Field of Search ........................................ 71/87

[56] References Cited
UNITED STATES PATENTS

| | | | |
|---|---|---|---|
| 2,959,610 | 11/1960 | Young et al. ................ | 260/461 |
| 3,102,023 | 8/1963 | Speziale et al. .............. | 71/87 |
| 3,134,801 | 5/1964 | Schring et al. ............... | 260/461 |

FOREIGN PATENTS OR APPLICATIONS 436,831  11/1967  Switzerland............... 71/87

*Primary Examiner*—Lewis Gotts
*Assistant Examiner*—Catherine L. Mills
*Attorney, Agent, or Firm*—Harry Falber

[57] ABSTRACT

New dithiophosphates of the formula I

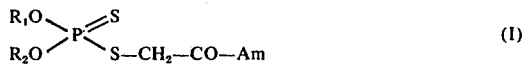

(I)

and their use as herbicides are disclosed. In formula I $R_1$ and $R_2$ are identical or different and each represents an alkyl or alkenyl or alkoxyalkyl radical with 1 to 5 carbon atoms, —CO—Am is an amide and Am is a piperidyl radical substituted by methyl or ethyl.

11 Claims, No Drawings

DITHIOPHOSPHATES AND THEIR USE AS HERBICIDES

Cross Reference

This is a division of applicaton Ser. No. 320,338, filed on Jan. 2, 1973, now U.S. Pat. No. 3,833,600, which in turn is a continuation-in-part of application Ser. No. 160,897 and 160,898, both filed on July 8, 1971, both now abandoned, both of which are continuations-in-part of application Ser. No. 782,736, filed Dec. 10, 1968, now abandoned.

The present invention relates to new dithiophosphates of the formula

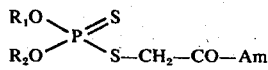

in which $R_1$ and $R_2$ are identical or different and each is an alkyl or alkenyl or alkoxyalkyl radical with up to 5 carbon atoms, —CO—Am is an amide and Am is a heterocyclic radical selected from the group consisting of 2-methyl-piperidine, 3-methylpiperidine, 4-methylpiperidine 2-ethylpiperidine and 2,6-dimethylpiperidine. The compounds of the formula I are prepared in a simple manner by reacting a halogenocarboxylic acid amide of the formula $$Hal - CH_2 - CO\ Am \qquad (II)$$

with a salt of a dithiophosphate of the formula

in a solvent. In these formulae, $R_1$, $R_2$ and Am have the meanings indicated, whereas Hal stands for halogen, especially chlorine, and Me for alkali, especially sodium or potassium, or $NH_4$. Accordingly, the acid forming the basis for the halogencarboxylic acid amides of the formula (II) are preferably chloroacetic acid. The solvents to be used are water or preferably an organic solvent, such as a lower aliphatic alcohol or a ketone having 1 to 4 carbon atoms in the aliphatic chain. The reaction temperature may vary between room temperature and the boiling temperature of the solvent. Depending on the nature of the reaction participants the addition of an alkali halide, for example sodium or potassium iodide, as catalyst may be of advantage.

Alternatively, for example an ester of an O,O-dialkyldithiophosphoryl acetic acid, for example the phenyl, benzyl or ethyleneglycol ester of such an acid may be reacted with the desired heterocycle. It is also possible to react (a) a mixed anhydride of such a phosphorylacetic acid, for example the anhydride with benzoic acid, with carbonic acid semiester, etc. with (b) the desired piperidine derivative. Alternatively, a salt, preferably an alkali metal salt, of such a phosphorylacetic acid may be reacted with a carboxylic acid chloride of the heterocycle and $CO_2$ eliminated at an elevated temperature.

The compounds of the formula I as such or in combination with a suitable additive can be used as selective herbicides or herbicidal compositions. Suitable additives are, for example solvents, diluents, dispersants, emulsifiers, thickening agents, adhesives and/or fertilizers, also other pest control agents, such as insecticides, acaricides, herbicides or fungicides.

As especially good acting agents in herbicidal controlling application have proved to be the dithiophosphates of the formula I wherein Am consists of a piperidyl group substituted by one methyl, the substituents $R_1$ and $R_2$ being identical. Among them compounds of the formula

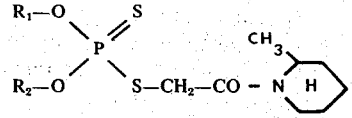

in which $R_1$ and $R_2$ are identical and each represents an alkyl or alkenyl radical with up to 4 carbon atoms; the preferred compounds being O,O-diethyl-dithiophosphoryl-aceto-2-methyl-piperidide and O,O-di-(n-propyl)-dithiophosphoryl-aceto-2-methyl-piperidine.

Selectivity is observed especially in the preemergence method against broadleaved weeds in cotton, soya, maize, wheat, rice and other crop cultures. This finding is surprising because many known, similarly constituted compounds (cf. for example German Pat. No. 819,998 where the unsubstituted amide, the anilide, the hydroxymethylamide, the butylamide of O,O-dialkyldithiophosphoryl-acetic or -propionic acids are described) have practically no herbicidal effect but are active against insects and mites.

The compositions which contain an active substance of the formula (I) can be applied in a great variety of forms, for example in the form of emulsions, dusting powders, dispersions, granules, etc. The mode of application depends exclusively on the intended use.

For the manufacture of sprayable solutions of the compounds of the general formula I there can be used for example mineral oil fractions of high to medium boiling range, such as Diesel oil or kerosene, coal tar oil and oils of vegetable or animal origin, as well as hydrocarbons, such as alkylated naphthalenes, tetrahydronaphthalene, if desired with the use of xylene mixtures, cyclohexanols, ketones, also chlorinated hydrocarbons, such as trichlorethane and tetrachlorethylene or tri- or tetrachlorobenzenes. Advantageously, organic solvents whose boiling point is above 100°C are used.

It is especially advantageous to prepare aqueous forms of application from emulsion concentrates, pastes, or wettable spraying powders by adding water. Suitable emulsifiers and dispersants are non-ionic, anion-active and cation-active products. Non-ionic products are as a rule condensation of aliphatic alcohols, amines or carboxylic acids which contain a longchain hydrocarbon radical with about 10 to 20 carbon atoms, with ethylene oxide, as for example the condensation product of octadecyl alcohol and 25 to 30 mols of ethylene oxide or that of commercial oleylamine and 15 mols of ethylene oxide, or that of dodecylmercaptan and 12 mols of ethylene oxide. Among the anion-active emulsifiers mention may be made of: the sodium salt of dodecyl alcohol sulfuric acid ester, the sodium salt of dodecylbenzenesulfonic acid, the potassium or triethanolamine salt of oleic acid or of abietic acid or of mixtures of these acids, or the sodium salt of a petroleum sulfonic acid. Suitable cation dispersants are quaternary ammonium compounds, such as cetyl pyridinium bromide or dioxyethylbenzyl-dodecylammonium chloride.

Solid carriers suitable for the manufacture of dusting and scattering preparations are talcum, kaolin, bentonite, calcium carbonate, calcium phosphate, attapulgit, bentonite, kaolin, $SiO_2$, polyacrylonitrile, and also carbon, corkmeal, woodmeal and other materials of vegetable origin. The manufacture of preparations in granular form is also very appropriate. As is usual in formulation practice, the various forms of application may contain substances which improve distribution, adhesion, rain resistance or penetration. Such substances are, for example, fatty acids, resins, glue, casein or alginates.

The dithiophosphates of this invention may also be used jointly with fertilizers. Quantities between 1 and 5 kg/ha may be used.

EXAMPLE 1

A suspension of 530 g (2 moles) of the K-salt of O,O-di-n-propyl-dithiophosphoric acid in 1000 ml of methanol is prepared, to which 316 g (1.8 moles) of N-chloroacetyl-2-methyl-piperidine is added dropwise while stirring. The reaction vessel is cooled so that the temperature of the reaction mixture remains between 25° and 30°C. Stirring is then continued for 2 hours at room temperature and for another hour at 40°C. Water is then added to the reaction mixture until all the KCl has dissolved. An oil separates which is taken up with 1000 ml of methylene chloride. The organic layer is separated, washed with water and dried over sodium sulfate. The methylene chloride is distilled and O,O-di-(n-propyl)-dithiophosphoryl-aceto-2-methyl piperidine remains as a yellowish oil (compound No. 3)

Analysis P calc: 8.76% P found: 9.0% $n_D^{20}$ 1.5258.

In a similar manner the following dithiophosphates were prepared:

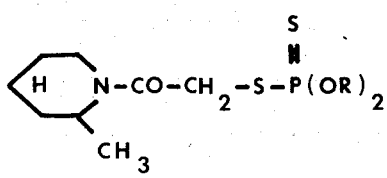

| No. | R | analysis | | $n_D^{20}$ |
|---|---|---|---|---|
| | | calc. | found | |
| 1 | methyl | P: 10.43% | 10.2% | 1.5446 |
| 2 | ethyl | P: 9.52% | 9.3% | 1.5332 |
| 3 | propyl | P: 8.76% | 9.0% | 1.5258 |
| 4 | allyl | P: 8.86% | 8.5% | 1.5430 |
| 5 | butyl | N: 3.67% | 4.0% | 1.5200 |
| 6 | 2-methoxy-ethyl | P: 8.04% | 7.5% | 1.5262 |
| 7 | 2-ethoxy-ethyl | P: 7.48% | 7.6% | 1.5204 |

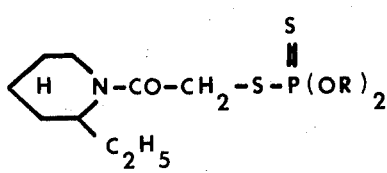

| No. | R | analysis P | | $n_D^{20}$ |
|---|---|---|---|---|
| | | calc. | found | |
| 3 | ethyl | 9.12% | 9.1% | 1.5306 |
| 9 | propyl | 8.43% | 8.3% | 1.5230 |

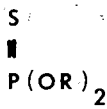

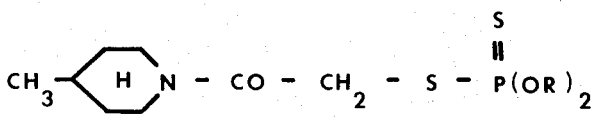

| No. | R | calculated P | found P | $n_{20}^D$ |
|---|---|---|---|---|
| 10 | ethyl | 9.52% | 9.5% | 1.5315 |
| 11 | propyl | 8.76% | 8.7% | 1.5235 |
| 12 | butyl | 8.12% | 8.1% | 1.5178 |
| 13 | 2-ethoxy-ethyl | 7.49% | 7.5% | 1.5184 |

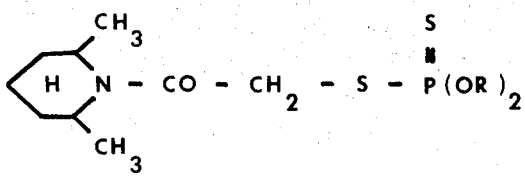

| No. | R | calculated | | found | | $n_{20}^D$ |
|---|---|---|---|---|---|---|
| | | P | N | P | N | |
| 14 | ethyl | 9.52% | | 9.5% | | 1.5310 |
| 15 | propyl | 8.76% | | 8.7% | | 1.5237 |
| 16 | allyl | | 4.01% | | 4.0% | 1.5387 |
| 17 | 2-methoxy-ethyl | | 3.63% | | 3.7% | 1.5248 |

| No. | R | calculated P | found P | $n_{20}^D$ |
|---|---|---|---|---|
| 18 | ethyl | 9.12 | 8.8 | |
| 19 | propyl | 8.43 | 8.4 | 1.5253 |
| 20 | allyl | 8.52 | 8.58 | 1.5429 |
| 21 | butyl | 7.83 | 8.0 | 1.5192 |
| 22 | 2-ethoxy-ethyl | 7.24 | 7.13 | 1.5206 |

EXAMPLE 2

Emulsion concentrate

A. The active substances which are readily soluble in organic solvents can be formulated as emulsion concentrates as follows:

20 parts of active substance
70 parts of xylene
10 parts of a mixture of a reaction product of an alkyl phenol with ethylene oxide and calcium dodecyl benzene sulfonate are mixed together. On dilution with water to the desired concentration a sprayable emulsion is obtained.

B. The active substance No. 1 is so dissolved in acetone that a 50% solution is obtained. A 25% solution in xylene of a 1:1 emulsifier mixture of Toximul MP and Toximul Q is added, and the whole is made up with xylene so that a 20% emulsion concentrate is formed. On dilution with water, a sprayable emulsion is obtained. (Toximul MP consists predominatly of calcium dodecyl benzene sulfonate, and Toximul Q predominantly of the condensation product of glycerine-diricinoleate and ethylene oxide).

EXAMPLE 3

Pre-emergence application on culture plants and weeds (I)

For the comparative test in a green house a spray broth was prepared by diluting a 25% emulsion concentrate of the active ingredient.

Pots of 10 cm diameter were filled with agricultural earth up to a height of 12 to 15 cm. The plants were seeded at a depth of 1 cm and then watered.

After one day the application of the active substance was carried out.

The temperature in the green house was then kept at 20°–25° C and the relative humidity at 70–80%.

The evaluation took place 4 weeks after treatment.

As comparative compounds were used:

compound A = O,O-dimethyl-S-(morpholino-carbonyl-methyl)-dithiophosphate of the formula

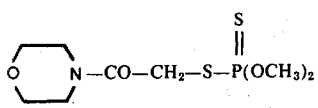

(known from Brit.Pat. Specification No. 814,587)

compound B = O,O-diethyl-S-(piperidino-carbonyl-methyl)-dithiophosphate of the formula

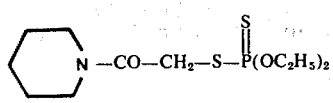

(according to U.S. Pat. No. 3,134,801).

EXAMPLE 4

Pre-emergence application on culture plants and weeds (II)

The following plants were sown in earthenware pots (in a hothouse):

culture plants:

| | |
|---|---|
| Sorghum | = Sorghum-millet |
| Triticum | = wheat |
| Hordeum | = barley |
| Avena | = oats |
| Zea | = maize |
| Oryza | = rice |
| Beta | = sugar beets |
| Glycine | = soya |
| Gossypium | = cotton | weeds

Digitaria
Panicum
Poa
Alopecurus
Cyperus
Galium
Amaranthus

A spray-broth containing the active substance was used in the pre-emergence process, 1 day after seeding, using 2 and 4 4 kg a.s. ha, respectively, and inspected 3 weeks later.

| Plants | Comp. No. 2 kg a.s. /ha 2 | | 1 | 0.5 | Comp. No. 3 kg a.s. /ha 2 | | 1 | 0.5 | B kg a.s. /ha 2 | | 1 | 0.5 | A kg a.s. /ha 2 | | 1 | 0.5 |
|---|---|---|---|---|---|---|---|---|---|---|---|---|---|---|---|---|
| Hordeum | 2 | 2 | 1 | | 3 | 1 | 1 | 1 | 1 | 1 | 1 | 1 | 1 | 1 |
| Oryza | — | 2 | 2 | | — | 2 | 2 | — | 1 | 1 | — | 1 | 1 |
| Gossypium | 1 | 1 | 1 | | 2 | 2 | 1 | 1 | 1 | 1 | 1 | 1 | 1 |
| Glycine | 3 | 2 | 2 | | 4 | 3 | 2 | 1 | 1 | 1 | 1 | 1 | 1 |
| Lolium perenne | 9 | 7 | 7 | | 9 | 8 | 7 | 1 | 1 | 1 | 1 | 1 | 1 |
| Alopercurus myos. | 9 | 9 | 7 | | 9 | 9 | 9 | 1 | 1 | 1 | 1 | 1 | 1 |
| Cyperus esculentus | 9 | 9 | — | | 9 | 9 | — | 1 | 1 | — | 1 | 1 | — |
| Rottboellia exelt. | 9 | 9 | 9 | | 9 | 9 | 8 | 1 | 1 | 1 | 1 | 1 | 1 |
| Digitaria sang. | 9 | 9 | 9 | | 9 | 9 | 9 | 1 | 1 | 1 | 1 | 1 | 1 |
| Echinochloa c.g. | 9 | 9 | 9 | | 9 | 9 | 9 | 2 | 2 | 1 | 1 | 1 | 1 |
| Sesbania exalt. | 8 | 4 | 1 | | 7 | 6 | 6 | 1 | 1 | 1 | 1 | 1 | 1 |
| Galium | 3 | 2 | 2 | | 5 | 4 | 4 | 1 | 1 | 1 | 1 | 1 | 1 |
| Amaranthus ret. | 9 | 8 | 6 | | 9 | 9 | 9 | 1 | 1 | 1 | 1 | 1 | 1 |

Legend:
1 = no damage to plant, same as control
2–3 = slight reversible damage
4–5 = medium damage
6–8 = heavy non-reversible damage
9 = plant completely destroyed

| Plant | Quantity used 4 kg/ha Active Substance No. | | | | | | | Quantity used 2 kg/ha Active Substance No. | | | | | | |
|---|---|---|---|---|---|---|---|---|---|---|---|---|---|---|
| | 1 | 3 | 18 | 2 | 4 | 5 | A | 1 | 3 | 18 | 2 | 4 | 5 | A |
| Triticum | 5 | 6 | 3 | 7 | 1 | 1 | 1 | 2 | 4 | 1 | 6 | 1 | 1 | 1 |
| Hordeum | 2 | 3 | 3 | 7 | 1 | 1 | 1 | 1 | 2 | 1 | 5 | 1 | 1 | 1 |
| Avena | 1 | 4 | 1 | 3 | 1 | 1 | 1 | 1 | 1 | 1 | 1 | 1 | 1 | 1 |
| Zea | 5 | 4 | 4 | 7 | 1 | 1 | 1 | 4 | 2 | 3 | 6 | 1 | 1 | 1 |
| Oryza | 9 | 4 | 3 | 7 | 1 | 1 | 1 | 4 | 2 | 1 | 5 | 1 | 1 | 1 |
| Digitaria | 9 | 9 | 9 | 9 | 9 | 9 | 1 | 9 | 9 | 9 | 9 | 9 | 9 | 1 |
| Sorghum | 8 | 7 | 7 | 8 | 7 | 1 | 1 | 3 | 6 | 3 | 6 | 6 | 1 | 1 |
| Panicum | 9 | 9 | 9 | 9 | 8 | 8 | 1 | 8 | 8 | 5 | 9 | 8 | 6 | 1 |
| Poa | 8 | 9 | 9 | 9 | 9 | 6 | 1 | 7 | 9 | 7 | 9 | 6 | 5 | 1 |
| Alopecurus | 6 | 9 | 5 | 7 | 9 | 8 | 1 | 3 | 8 | 1 | 6 | 8 | 5 | 1 |
| Cyperus | 8 | 9 | 6 | 9 | 9 | 1 | 1 | 7 | 9 | 4 | 8 | 7 | 1 | 1 |
| Beta | 2 | 3 | 3 | 1 | 1 | 1 | 1 | 2 | 1 | 1 | 1 | 1 | 1 | 1 |
| Galium | — | — | 3 | 1 | 1 | 1 | 1 | — | — | 1 | 1 | 1 | 1 | 1 |
| Gossypium | 1 | 1 | 1 | 1 | 1 | 1 | 1 | 1 | 1 | 1 | 1 | 1 | 1 | 1 |
| Amaranthus | 1 | 9 | 1 | 5 | 3 | 1 | 1 | 1 | 9 | 1 | 8 | 3 | 1 | 1 |
| Glycine | 3 | 2 | 1 | 5 | 1 | 1 | 1 | 1 | 1 | 1 | 3 | 1 | 1 | 1 |

A = O,O-dimethyl-S-(morpholino-carbonyl-methyl)-dithiophosphate known from the British Patent No. 814,587

Legend
1 = no damage to plant, same as control
2–3 = slight reversible damage
4–5 = medium damage
6–8 = heavy non-reversible damage
9 = plant completely destroyed

EXAMPLE 5

Post-emergence application on Echinochloa is seeded paddy-rice.

In a green house, asbestos trays of size 60 × 60 cm were seeded with rice and Echinochloa. The earth in the trays was kept very humid and 8 days after seeding, when the Echinochloa plants were in the 2-leaf stage, the culture was submerged under a 2 cm deep layer of water. Active substance in the form of a 7,5 % granulate was then added to the trays in an amount corresponding to 0.5, 1,2 and 4 kg of active substance per hectare. 25 days after this treatment the test was evaluated according to the following key
1 plants unharmed, as in control
2-3 slight reversible damage to plants
4-5 medium damage
6-8 heavy non reversible damage
9 plant completely destroyed.
The results are summarized in the table below

| compound | amount applied in kg/ha | effect on seeded rice | Echinochloa |
|---|---|---|---|
| 3 | 1 | 1 | 9 |
|   | 2 | 1 | 9 |
|   | 4 | 1 | 9 |
| 8 | 0.5 | 1 | 9 |
|   | 1 | 3 | 9 |
|   | 2 | 7 | 9 |
| 9 | 0.5 | 1 | 9 |
|   | 1 | 1 | 9 |
|   | 2 | 1 | 9 |
| S-ethyl-hexahydro-1H-1-carbothioate ="molinate" | 0.5 | 1 | 3 |
|   | 1 | 1 | 5 |
|   | 2 | 1 | 7 |

Post-emergence application on Echinochloa in transplanted paddy-rice

In a similar test, 25 days old rice plants were transplanted in a green house into earth filled asbestos trays of a size 60 × 60 cm. Echinochloa was then seeded into this culture. The earth was kept very humid and after 12 days, when the Echinochloa-plants had reached the 2-3 leaf stage, the culture in the trays was submerged under a 2,5 cm deep layer of water. The active substance was then added to the trays in the form of a 7.5% granulate, in an amount correspondng to 0.5, 1 and 2 kg of active substance per hectare. The test was evaluated a 25 days after this treatment according to the key given above. The results are summarized in the table below.

| compound | amount applied in kg/ha | effect on transplanted rice | Echinochloa |
|---|---|---|---|
| 3 | 0.5 | 1 | 9 |
|   | 1 | 1 | 9 |
|   | 2 | 1 | 9 |
| S-ethyl-hexahydro-1H-azepine-carbothioate ="molinate" | 1 | 1 | 6 |
|   | 2 | 1 | 9 |

What we claim is:
1. A herbicidal composition for combatting weeds in crop cultures which comprises a herbicidally effective amount of a compound of the formula

$$R_1-O\diagdown P\diagup S \atop R_2-O\diagup \diagdown S-CH_2-CO-Am$$

wherein $R_1$ and $R_2$ are identical or different and each is an alkyl, alkenyl or alkoxyalkyl radical with up to 5 carbon atoms; and Am is a heterocyclic radical selected from the group consisting of 2-metylpiperidine, 3-methylpiperidine, 4-methylpiperidine and 2,6-dimethylpiperidine; together with a suitable carrier therefor.

2. The composition of claim 1, wherein in said compound Am is a piperidyl group substituted by one methyl.

3. The composition of claim 2, wherein said compound is $$R_1-O\diagdown P\diagup S \atop R_2-O\diagup \diagdown S-CH_2-CO-N\text{(4-methylpiperidyl)}$$

wherein $R_1$ and $R_2$ are identical and each represents an alkyl or alkenyl radical with up to 4 carbon atoms.

4. The composition of claim 3, wherein said compound is $$(H_5C_2O)_2-\overset{S}{\underset{\|}{P}}-S-CH_2-CO-N\text{(4-methylpiperidyl)}$$

5. The composition of claim 3, wherein said compound is $$(n-H_7C_3O)_2-\overset{S}{\underset{\|}{P}}-S-CH_2-CO-N\text{(4-methylpiperidyl)}$$

6. A method for combatting weeds in crop cultures which comprises applying to the crop area a herbicidally effective amount of a compound of the formula according to claim 1.

7. The method of claim 6, wherein in said compound Am is a piperidyl group substituted by one methyl.

8. The method of claim 7, wherein said compound is $$R_1-O\diagdown P\diagup S \atop R_2-O\diagup \diagdown S-CH_2-CO-N\text{(4-methylpiperidyl)}$$

wherein $R_1$ and $R_2$ are identical and each represents an alkyl or alkenyl radical with up to 4 carbon atoms.

9. The method of claim 8, wherein said compound is $$(H_5C_2O)_2-\overset{S}{\underset{\|}{P}}-S-CH_2-CO-N\text{(4-methylpiperidyl)}$$

10. The method of claim 8, wherein said compound is
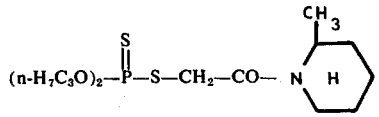
11. The method of claim 6, wherein said compound is applied to rice cultures.
* * * * *